(12) United States Patent
Schuster

(10) Patent No.: US 7,154,992 B2
(45) Date of Patent: Dec. 26, 2006

(54) PHASE CONTRAST X-RAY DEVICE FOR CREATING A PHASE CONTRAST IMAGE OF AN OBJECT AND METHOD FOR CREATING THE PHASE CONTRAST IMAGE

(75) Inventor: Manfred Schuster, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/673,170

(22) Filed: Sep. 30, 2003

(65) Prior Publication Data

US 2004/0062349 A1 Apr. 1, 2004

(30) Foreign Application Priority Data

Sep. 30, 2002 (DE) ................ 102 45 676

(51) Int. Cl.
*G01N 23/20* (2006.01)
(52) U.S. Cl. ...................................... 378/79
(58) Field of Classification Search ............ 378/70–90
See application file for complete search history.

(56) References Cited

U.S. PATENT DOCUMENTS

| 4,945,552 | A |  | 7/1990 | Ueda et al. ............... 378/99 |
| 5,319,694 | A |  | 6/1994 | Ingal et al. ............... 378/84 |
| 5,579,363 | A |  | 11/1996 | Ingal et al. ............... 378/84 |
| 5,715,291 | A |  | 2/1998 | Momose ................ 378/84 |
| 6,594,335 | B1 | * | 7/2003 | Davidson ............... 378/43 |
| 2001/0038680 | A1 |  | 11/2001 | Davidson ............... 378/43 |

FOREIGN PATENT DOCUMENTS

| EP | 0 539 608 A1 | 5/1993 |
| EP | 0 784 202 A2 | 7/1997 |
| EP | 0 818 131 B1 | 10/2004 |
| WO | WO 95/05725 A1 | 2/1995 |
| WO | WO 96/31098 A1 | 10/1996 |

OTHER PUBLICATIONS

S.W. Wilkins et al., "Phase-Contrast Image Using Polychromatic Hard X-Rays," Nature, V. 384, 1996, pp. 335-338.
M. Schuster et al., "Laterally Graded Multilayer Optics for X-Ray Analysis," Proc. SPIE, V. 3767, 1999, pp. 183-198.
F.S. Crawford, Jr., "Schwingungen und Wellen," Vieweg, Braunschweig, 1989, pp. 259-271.
L.M.N. Távora et al., "Optimisation of Transmission Target X-Ray Tubes for Imaging Applications using Monte Carlo Based Methods," SPIE, V. 3771, 1999, pp. 61-71.

(Continued)

*Primary Examiner*—Edward J. Glick
*Assistant Examiner*—Jurie Yun
(74) *Attorney, Agent, or Firm*—Young & Thompson

(57) ABSTRACT

The invention concerns a phase contrast X-ray device for creating a phase contrast image of at least one object with at least one X-ray source for generating an X-radiation that has a specific spatial coherence within a specific optical distance to the X-ray source and at least one evaluation unit for converting the X-radiation after the X-radiation has passed through the object arranged within the optical distance to the X-ray source in the phase contrast image of the object. The X-ray source has an output ranging from 50 W up to and including 10 kW and a spatial coherence length of the X-radiation has been selected within the optical distance to the X-ray source ranging from 0.05 μm.

18 Claims, 6 Drawing Sheets

OTHER PUBLICATIONS

M.A. Piestrup et al., "A Design of Mammography Units Using a Quasimonochromatic X-Ray Source," Review of Scientific Instruments, V. 72, 2001, pp. 2159-2170.

V.G. Baryshevsky et al., "A Comparative Analysis of Various Mechanisms for the Generation of X-Rays by Relativistic Particles," Nuclear Instruments and Methods in Physics Research, V. 228, 1985, pp. 490-495.

Wolfgang Knüpfer et al., "Channelingstrahlung," Physik in unserer Zeit, V. 6, 1984, pp. 163-172.

Akira Tsunemi et al., "Backward Compton Scattering of Picosecond $CO_2$ Laser Pulses Using Relativistic Electron Beam for the Bright X-Ray Generation," IEEE, V. 3, 1999, pp. 926-927.

Akira Tsunemi et al., "Ultra-Bright X-Ray Generation using Inverse Compton Scattering of Picosecond $CO_2$ Laser Pulses," IEEE, V. 4, 1999, pp. 2552-2554.

* cited by examiner

US 7,154,992 B2

PHASE CONTRAST X-RAY DEVICE FOR CREATING A PHASE CONTRAST IMAGE OF AN OBJECT AND METHOD FOR CREATING THE PHASE CONTRAST IMAGE

FIELD OF THE INVENTION

The invention relates to a phase contrast X-ray device for creating a phase contrast image of at least one object with at least one X-ray source for generating an X-radiation that exhibits a specific spatial coherence within a specific optical distance to the X-ray source and at least one evaluation unit for converting the X-radiation after the X-radiation has passed through the object arranged within the optical distance to the X-ray source in the phase contrast image of the object. A method for creating a phase contrast image of an object by using the phase contrast X-ray device is also described.

BACKGROUND OF THE INVENTION

In the same way as in the visible light optical range, the X-ray optical range must also convert a phase contrast to an amplitude contrast to make a phase contrast object visible. Therefore, a phase contrast image means a graphical representation of a phase contrast converted to an amplitude contrast. However, images of objects are considered throughout in which the contrast image is actually based on phase contrast and not amplitude contrast.

The phase contrast radiography underlying the invention is based on the fact that X-rays which pass through a phase contrast object, i.e. through adjacent ranges of different optical thickness, have a well-defined phase difference to one another. Therefore, these X-rays can interfere with one another (X-ray interference). As a result of this X-ray interference, an amplitude or intensity contrast image is observed at a sufficient distance. The interference is also related to a deflection of the radiation to the direction of incidence (diffraction). The above-mentioned phase contrast object can be seen as a transparent object with one lateral variation of the thickness, the refractive index or both. In contrast to the X-ray absorption radiography, an image of an object can be generated with the phase contrast radiography which has a lower absorption for X-rays and small absorption contrasts based on the thickness, the density or the element composition.

A phase contrast X-ray device of the kind mentioned at the beginning and an appropriate method is e.g. known from Wilkins et al., Nature, 384 (1996), pages 335–338 (cf. FIG. 2). The X-ray source of the known X-ray device is point-shaped and has a very small diameter from 5 μm to 15 μm. The evaluation unit is, for example, an X-ray film. The object to be investigated is arranged within the optical distance to the X-ray source between the point-shaped X-ray source and the evaluation unit. The optical distance results from a ray path of the X-radiation. Divergent X-rays radiated from the point-shaped X-ray source pass through the object. At a phase limit of the object, a passing through of the object causes a phase shift of the X-radiation. Both phase-shifted and non-phase shifted X-rays reach the evaluation unit, are converted to an amplitude contrast there and made visible as a so-called phase contrast image.

Based on the smaller diameter of the point-shaped X-ray source of the known phase contrast X-ray device, a (radiographic) output of the X-ray source is restricted to below 50 W. Because of the lower output, the phase contrast X-ray device is suitable for creating a phase contrast image of a thin, small object, for example an insect. The known phase contrast X-ray device is not suitable for larger and thicker objects, for example a human being, because of the lower output. Therefore, the phase contrast X-ray device is also not suitable for use in medical technology.

A monochromator as a gradient multilayer reflector is known from Schuster et al., Proc. SPIE, 3767 (1999), pages 183–198. The gradient multilayer reflector is an artificial, one-dimensional grid that allows the Bragg area of reflection of X-radiation. The reflector distinguishes itself by means of a periodic series of layers of a first layer type A and a further layer type B. The first layer type A has a first refractive index $r_A$ and a first layer thickness $d_A$ and a further layer thickness B, a further refractive index $r_B$ and a layer thickness $d_B$ differing from the first refractive index $r_A$. In one lateral direction of propagation of the reflector, the layer thicknesses increase by a total of $d=d_A+d_B$. The gradient multilayer reflector then has an area of reflection that can be elliptical, parabolic, circular or planar.

The gradient multilayer reflector is used, for example, as a mirror in X-ray diffractometry. By using this gradient multilayer reflector, parallel and nonparallel X-radiation of a relatively great photon energy bandwidth can be reflected and can be monochromated with a relatively small intensity loss.

SUMMARY OF THE INVENTION

The object of the present invention is to specify an improved phase contrast X-ray device compared to the known prior art by means of which a phase contrast image of a larger or thicker object can be created. Another object is to specify an improved method for creating a phase contrast image compared to the known prior art.

In order to achieve the object of the invention, a phase contrast X-ray device is specified for creating a phase contrast image of at least one object with at least one X-ray source for generating an X-radiation that has a specific spatial coherence within the specific optical distance to the X-ray source and at least one evaluation unit for converting the X-radiation after the X-radiation has passed through the object arranged within the optical distance to the X-ray source in the phase contrast image of the object. The phase contrast X-ray device is characterized in that the X-ray source has an output ranging from 50 W up to and including 10 kW and a spatial coherence length of the X-radiation has been selected within the optical distance to the X-ray source ranging from 0.05 μm up to and including 10 μm.

In order to achieve the further object of the invention, a method for creating a phase contrast image of an object by using the phase contrast X-ray device is given with the following procedural steps:

a) Arranging the object within the optical distance to the X-ray source,
b) X-radiation passing through the object and
c) Creating the phase contrast image from where the X-radiation passes through an object by means of the evaluation unit.

The object is characterized by at least one boundary surface that can be made visible with the phase contrast image. The boundary surface is, for example, formed by different, adjacent parts of the object. These parts can be, for example, different vessels of a plant or an animal.

The evaluation unit features a detector for the X-radiation passing through the object. The detector is, for example, an X-ray film. An X-ray tracer or an X-ray tracer carrier that converts the X-radiation into visible light is also feasible. The phase contrast image is created from the visible light.

The basic idea of the invention is to prepare a phase contrast X-ray device with an X-ray source for X-radiation in which case the X-radiation has an X-radiation within the optical distance to the X-ray source that is suitable for recording a phase contrast image of an object. For that, the X-radiation has a specifically suitable spatial coherence within the optical distance for recording a phase contrast image. The spatial coherence also becomes a transversal coherence. The spatial coherence length of the X-radiation is only a few µm within the optical distance. Over and above this basic requirement for recording a phase contrast image, the X-ray source output must be selected in such a way that it is between 50 W and 10 kW. Therefore, the output is higher than that of the known phase contrast X-ray device. The phase contrast X-ray device is suitable for creating a phase contrast image of both a smaller object, for example, an insect and a larger object, for example, a human being. A recording period of the phase contrast image is also acceptable for larger objects. Therefore, the phase contrast X-ray device can also be used in medical technology, for example, in a laboratory or a hospital. Using the phase contrast X-ray device in botany, the semiconductor technology and the microstructure technology is also feasible. For example, in semiconductor technology, a thin bonding wire of aluminum on a silicon chip could be shown. Application in safety engineering for testing a safety-relevant object is also feasible. The safety-relevant object is, for example, a bag whose contents are to be shown by means of the phase contrast X-ray device. The contours of explosives or drugs could be rendered visible in the phase contrast image.

Measures based on special embodiments by means of which the basic idea of the invention is developed further are given below.

In a special embodiment, the X-ray source has a line-shaped focus. The focus is elongated. A focus length of the focus is considerably greater than a focus width of the focus. The focus can then also have a rectangular focus area. An elliptical focus area is also feasible. For example, the focus width is only a few µm and the focus length, on the other hand, is up to several mm. The line-shaped focus allows a considerably higher tube output and therefore a higher intensity than a comparable tube with point-shaped focus.

In a further embodiment, a longitudinal extension of the line-shaped focus is actually aligned in the direction towards the object. The longitudinal extension is determined by the focus length. The direction of the object is given by the light path of the X-radiation from the X-ray source to the object. The alignment of the focus is elongated. The elongated alignment guarantees a useable spatial coherence length (cf. F. S. Crawford Jr., "Schwingungen und Wellen" (Oscillations and Waves) (Vieweg, Braunschweig, 1989), pages 259–271).

For example, an X-ray source is used together with a conventional X-ray tube. The X-ray tube resembles a fine focus or finest focus from X-ray diffractometry. In contrast to X-ray diffractometry, the alignment of the line-shaped focus is elongated. For such a flat measurement, an anode roughness in the (sub)µm range is suitable.

In a special embodiment, the X-ray source has an X-ray tube with a transmission anode. The X-ray tube is a transmission X-ray tube. For this type of X-ray tube, the X-radiation is measured from the anode in the direction of bombardment of the electrons—therefore, in transmission (cf. L. M. N. Tavora, E. J. Morton, W. B. Gilboy, SPIE vol 3771 (1999) 61–71). Very often, in the case of transmission X-ray tubes, the anode is used at the same time as the tube window.

In a special embodiment, the X-ray source has a parametric X-radiation source. The parametric X-radiation source is a very efficient and powerful X-radiation source that can also be fitted in the described X-radiation device. In the case of a parametric X-radiation source, electrons are bombarded typically with 50 MeV into a monocrystalline anode material, e.g. graphite, diamond or beryllium. Therefore, X-radiation emerges that is considerably intensified if it is measured under the Bragg angle corresponding to the X-radiation.

Parametric X-radiation (PXR: parametric x-radiation, cf. M. A. Piestrup, Xizeng Wu, V. V. Kaplan, S. R. Uglov, J. T. Cremer, D. W. Rule, R. B. Fioroto, Rev. Sci. Intrum. 72 (2001) 2159–2170) is a type of X-radiation from many different X-radiation types, the generation process of which is very similar, but the generation of which requires different operating parameters. These X-radiation types are, for example, coherent X-radiation in crystals (CBS), Vavilov-Cerenkov radiation (VR), channeling radiation (CHR) and resonant radiation (RR) (cf. V. G. Baryshevsky, I. D. Feranchuk, Nucl. Instr. Meth. 228 (1985) 490–495; W. Knupfer, M. G. Huber, Physik in unserer Zeit 6 (Physics in our time 6) (1984) 163–172). These types of X-radiation can be used in the phase contrast X-ray device of this invention.

In addition to the X-ray sources described, an electron-excited plasma X-ray source or a laser-excited plasma X-ray source (laser Compton scattering) is feasible (cf. A. Tsunemi et al. IEEE 3 (1999) 926–927; A. Tsunemi et al. IEEE 4 (1999) 2552–2554).

In a further embodiment, the X-radiation of the phase contrast X-ray device displays a specific temporal coherence. The temporal coherence is also designated as the longitudinal coherence or monochromatism. Therefore, a temporal coherent X-radiation is a monochromatic X-radiation of a smaller bandwidth. In order to generate the temporal coherence, the phase contrast X-ray device has at least one monochromator. The monochromator filters X-radiation of a specific wave length $\lambda$ or a specific energy E from the polychromatic X-radiation of the X-ray source. The monochromator is arranged in the light path of the X-radiation between the X-ray source and the optical distance. Therefore, monochromatic X-radiation passes through the object. The coherence of the temporal X-radiation is particularly advantageous for creating phase contrast images of thicker objects. Thicker objects are objects whose extension in the direction of propagation of the X-radiation is clearly greater than the coherence length of the X-radiation. The coherence length is, for example, only a few µm and the thickness of the object, on the other hand, up to several mm or cm.

In order to be able to distinguish the phase shift of objects with a thickness T from those with a multiple thickness T*n, the thickness is preferably less than $\lambda/2\delta$. To prevent an ambiguity in the interferences, it is advantageous if a fluctuation of the wave length $\lambda$ and the refractive index decrement $\delta$ is small.

The evaluation unit comprises at least a film or an X-ray detector with selective area analysis capabilities. The evaluation unit also preferably has an analyzer for analyzing the direction of propagation after the X-radiation has passed through the object. The analyzer can then have a collimator. The analyzer particularly has a monochromator or resembles a monochromator. Whereas the wavelength of the photons is determined with a monochromator, the direction of propagation/collimation of the photons is determined with an analyzer.

In a special embodiment, the monochromator and/or analyzer has at least one gradient multilayer reflector. The reflector distinguishes itself by means of a periodic series of layers of a first layer type A and a further layer type B. The first layer type A has a first refractive index $r_A$ and a first layer thickness $d_A$ and a further layer thickness B, a further refractive index $r_B$ and a layer thickness $d_B$ differing from the first refractive index $r_A$. In at least one lateral direction of propagation of the reflector, the layer thicknesses increase by a total of $d=d_A+d_B$. By using the gradient multilayer reflector, parallel and non-parallel X-radiation can be monochromated or collimated with a relatively small intensity loss. The gradient multilayer reflector then has an area of reflection that can be elliptical and/or parabolic and/or planar and/or circular. The area of reflection either curves in only one direction of propagation or in two propagation directions of the gradient multilayer reflector. Because an area of reflection curves in two propagation directions of the gradient multilayer reflector it is possible not to only deflect the radiation in the plane of the arriving X-radiation, but also to change the plane of the reflecting X-radiation. Therefore, a spatial focusing can be obtained.

A spatial coherence needed to record the phase contrast image can, in particular, be accessed by using the gradient multilayer reflector. By using the reflector, the light path in which the object is arranged can be developed in parallel or divergently. A divergent light path can be obtained with a planar area of reflection. In the case of an elliptical or circular area of reflection, a focused light path is obtained. A parabolic area of reflection collimates the light path, i.e. the X-rays run in parallel.

In particular, another monochromator as a gradient multilayer reflector is used as an analyzer. The analyzer is suitable for a special embodiment of the invention after an X-radiation which is deflected when passing through the object for creating a phase contrast image and/or an X-radiation which is non-deflected when passing through the object is detected. The deflected and/or non-deflected X-radiation is selected by means of an analyzer with a gradient multilayer reflector. For example, at the reflector only the non-deflected X-radiation is guided in the direction of the detector of the evaluation unit.

In a special embodiment, the X-radiation forms an interference pattern after it has passed through the object that is detected for creating the phase contrast image. The interference pattern, for example, is recorded on an X-ray film.

In a special embodiment, several phase contrast images are created by means of the X-radiation of different spatial coherences that are processed to an overall phase contrast image by means of an image processing unit. For example, the individual phase contrast images are digitized and then converted by the image processing unit into the overall phase contrast image. It is also feasible that the individual phase contrast images are recorded with a single X-ray film and are superimposed onto an overall phase contrast image in this way.

A greater coherence length brings about a stronger diffraction effect and allows a higher phase contrast and sharper boundaries. However, complicated object structures can superimpose the diffraction patterns of different object structures that are difficult to interpret. For a smaller coherence length, the phase contrast is less and, on the other hand, the phase contrast of specific object structures can be allocated in a simpler manner. Without image processing, phase contrast images with greater coherence lengths can possibly no longer be determined. However, image processing programs also supply artifacts if a phase contrast image should be processed with a greater coherence length. Therefore, a repetitive evaluation algorithm is proposed in which the rough contours/boundaries of the object structures are first of all recorded in images with smaller coherence lengths and then these contours/boundaries are refined by means of images with a greater coherence length.

The optical distance between the object and the X-ray source preferably varies for generating the different spatial coherence. The spatial coherence length is then enlarged in both dimensions to the same extent with the distance.

As an alternative, orientation of the object to the direction of propagation of the X-radiation varies for generating the different spatial coherence. For example, the object is rotated in the case of an unchanged light path. One requirement for this is an anisotropy of the spatial coherence length, i.e. that the spatial coherence length differs in the two transversal directions.

It is indeed also feasible that the object remains laboratory proof, but that the anisotropic alignment is turned at an angle, by for example varying the two lateral extensions of the X-ray source. The focus and therefore also an X-ray source form can be changed in an X-ray tube.

This method preferably uses an object that, in essence, consists of a material with a low absorption coefficient for the X-radiation. Such an object or a part of the object cannot be shown directly, i.e. by using X-ray absorption. This object or a part of the object can be any soft part of humans, an animal or a plant. The soft part, for example, is a vessel of a body fluid of an animal. Organs that are not in a position to record a radioopaque medium needed to directly create an X-ray absorption image can, in particular, also be shown by means of the visualized phase contrast X-ray devices. Such organs are, for example, cartilages or periosteum.

In a further embodiment, many phase contrast images of the object are recorded to create a phase contrast computer tomogram of the object. Although the phase contrast X-ray radiography can also generate a sufficient contrast when there is no absorption contrast, the local details—as is customary for a projection technology—can only be shown superimposed. The method of computer tomography overcomes this problem: The object to be tested is scanned linearly and turned at slight angles throughout the process. A transversal sector tomogram is then generated from the position and angle-dependent intensities according to the well-known process of computer tomographic reconstruction.

Summarizing, the following exceptional advantages result from this invention:

Based on the higher tube output, this phase contrast X-ray device presented can, in particular, be used in medical technology for showing the soft parts of larger objects.

By using an X-ray source with line-shaped focus and/or by using one or several gradient multilayer reflectors, the intensity of the X-radiation within the optical distance increases or is used more efficiently.

Via the shape and alignment of the X-ray source, the spatial coherence of the X-radiation suitable for creating a phase contrast image can be ensured.

By using the gradient multilayer reflector, monochromating and also the temporal coherence of the X-radiation can be obtained with small intensity losses. Based on the temporal coherence, the phase contrast images of thicker objects can be accessed.

A gradient multilayer reflector, in particular, is used as an analyzer. With the reflector, the X-radiation that has passed through the object can be analyzed in a simple way.

BRIEF DESCRIPTION OF THE DRAWING

Based on several examples and the appropriate figures, the phase contrast X-ray device and the method for creating the phase contrast image of an object is shown by means of the phase contrast X-ray device. The figures are diagrammatic and do not display images to scale.

DETAILED DESCRIPTION OF THE INVENTION

Figure 2:
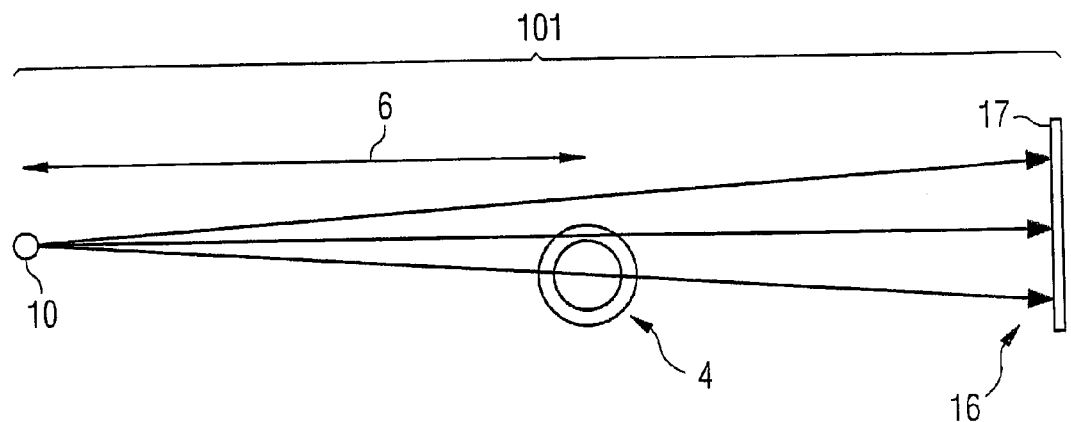
FIG. 2 shows the cross-section of a phase contrast X-ray device known from the state of the art.

The phase contrast X-ray device 101 known from the state of the art that is described in the introduction is shown in FIG. 2. Taking the point-shaped X-ray device 2 as a starting basis, the divergent X-rays 11 arrive at the object 4 arranged within the optical distance 6 to the X-ray source 2. After the X-radiation 11 has passed through the object 4, non-deflected, deflected and X-radiation 12 and 13 arrive at an evaluation unit 16 as an X-ray film by means of which the phase contrast image is generated. In order to obtain sufficient coherence length 15 for recording a phase contrast image, the diameter of the point-shaped X-ray source 2 is restricted and therefore the output of the X-ray source 2 is also limited to a maximum of 50 W.

Figure 7:
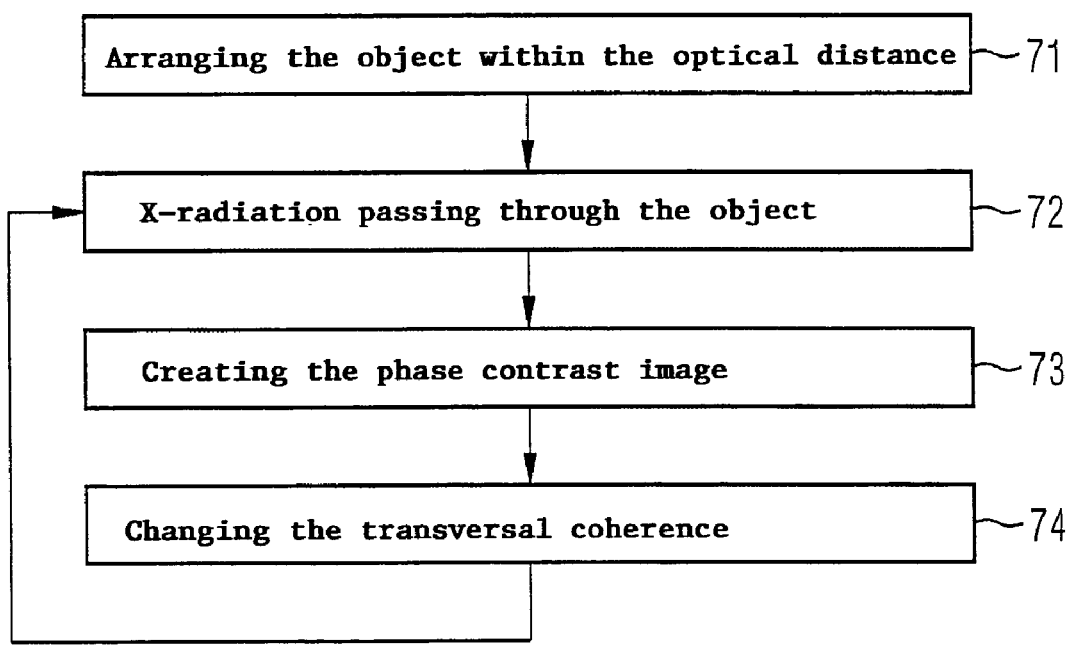
FIG. 7 shows a method for creating a phase contrast image by means of the phase contrast X-ray device.

On the other hand, the output of X-ray source 2 of this phase contrast X-ray device 1 exceeds 50 W. By means of the phase contrast X-ray device 1, a phase contrast image of an object 3 is created in each case. The object is cartilage on a bone. For that, the object 3 is arranged within the optical distance 6 to the X-ray source 2 (FIG. 7, 71). The object distinguishes itself with boundary surfaces 5 that can be shown by means of phase contrast radiography. After arranging, X-radiation passes through the object (FIG. 7, 71) and the phase contrast image is created from the X-radiation passing through the object by means of the evaluation unit 16. The evaluation unit 16 also has an X-ray film by means of which the X-radiation is detected. A phase contrast image is created.

In an embodiment of the method for creating the phase contrast image, the spatial coherence of the X-radiation used is changed gradually by varying the optical distance (FIG. 7, 74). In this way, several phase contrast images are created with X-radiation having different spatial coherence. These different phase contrast images are digitized and processed by means of an image processing unit into an overall phase contrast image.

According to a further embodiment of the method, many phase contrast images are generated by turning the object. A phase contrast tomogram is created from the many phase contrast images via an image processing device.

The way in which the output of the X-ray source 2 of the phase contrast X-ray device 1 can be increased and an image quality of the phase contrast image that can be created with this, can be increased, is described below. In essence, two routes are then followed: According to the first route, the phase contrast X-ray device 1 is equipped with an X-ray source 2 with line-shaped focus 7 (example 1). The second route provides an optical system in the light path to optimize the radiation intensity and the spatial coherence 14 and, if required, the temporal coherence 15 of the X-radiation 11 (examples 2 to 7).

EXAMPLE 1

Figure 1:
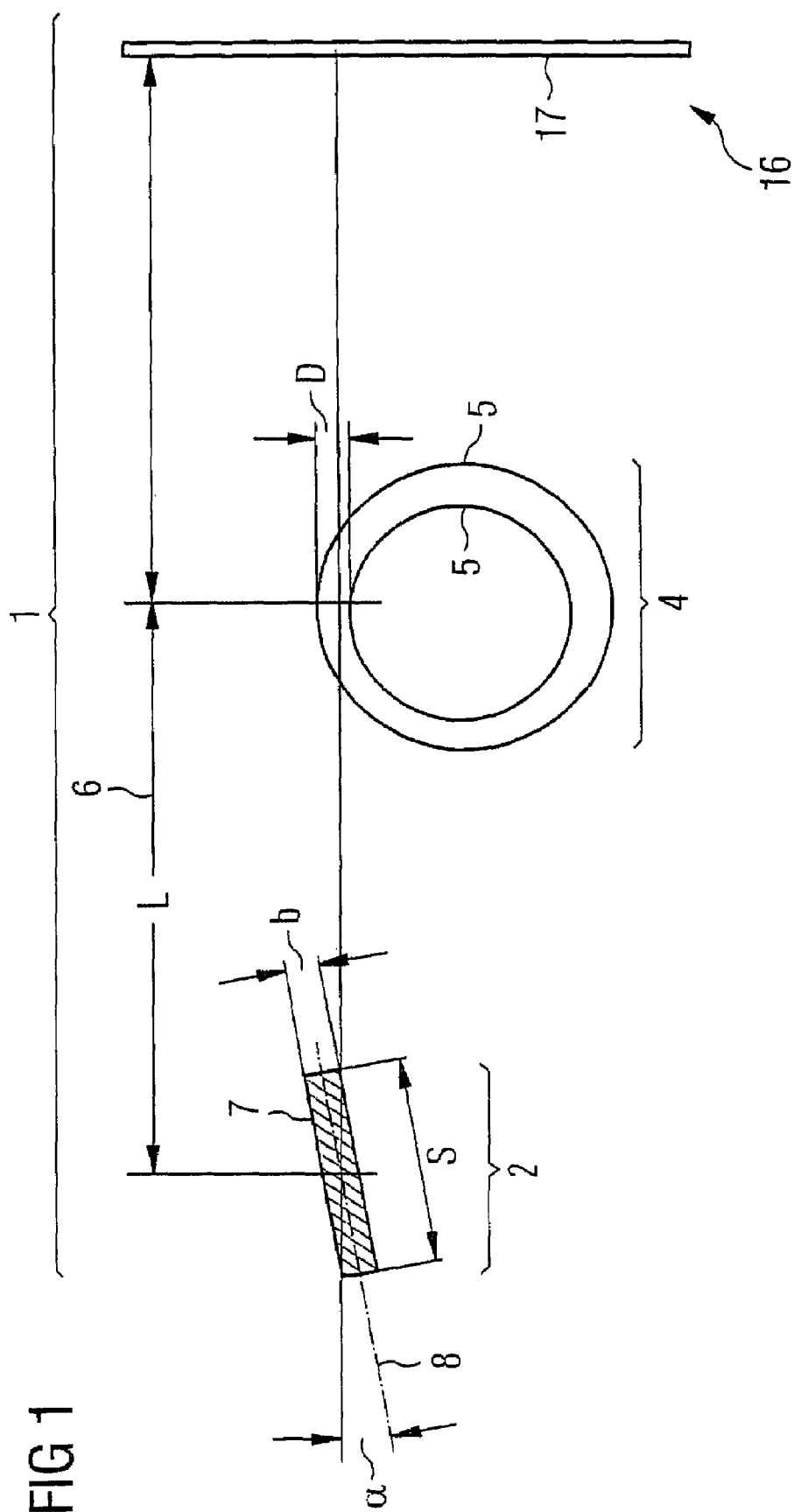
FIG. 1 shows the cross-section of a phase contrast X-ray device with an X-ray source with line-shaped focus.

Phase contrast X-ray device 1 with X-ray source 2 with line-shaped focus 7 (FIG. 1).

The X-ray source 2 has a line-shaped focus 7. The X-ray source 2 has an output of 1500 W within the optical distance 6 in which the object 4 to be investigated is arranged.

The longitudinal alignment 8, i.e. the focus length (longitudinal extension) of the focus 7 is aligned along two boundary surfaces 5 of the object 4. For a required phase contrast, the condition $\sin \alpha \ll \lambda \cdot L/D \cdot s$ is aligned in which case the angle $\alpha$ corresponds to an angle deviation of the focus longitudinal direction of the tangential surface boundary that should be made visible, s is the focus length of the focus, b the focus width of the focus, $\lambda$ the wave length of the X-radiation, L the optical distance between the focus of the X-ray source and the surface boundaries of the object and D a minimum distance between the surface boundaries 5 to be shown. The minimum distance D between the surface boundaries to be shown corresponds to the spatial coherence length 14. With $\lambda=0.070$ nm, s=2 µm, b=10 µm, L=1 m and D=1 µm it thus follows that b<<70 µm and a<<2°. In order to record the phase contrast image, the focus width b is clearly less than 70 µm. For a focus length s of 2 mm the alignment is more exact than 2°.

Focus 7 can easily be aligned if it is known how the boundary surfaces 5 to be shown are oriented. If an orientation of the boundary surfaces 5 to one another is unknown, several phase contrast images are recorded to determine the optimum alignment. A good alignment can be seen in a clear phase contrast. The searched for boundary surfaces 5 lead to clear borders of light and dark lines in the phase contrast image.

EXAMPLE 2

Figure 4:
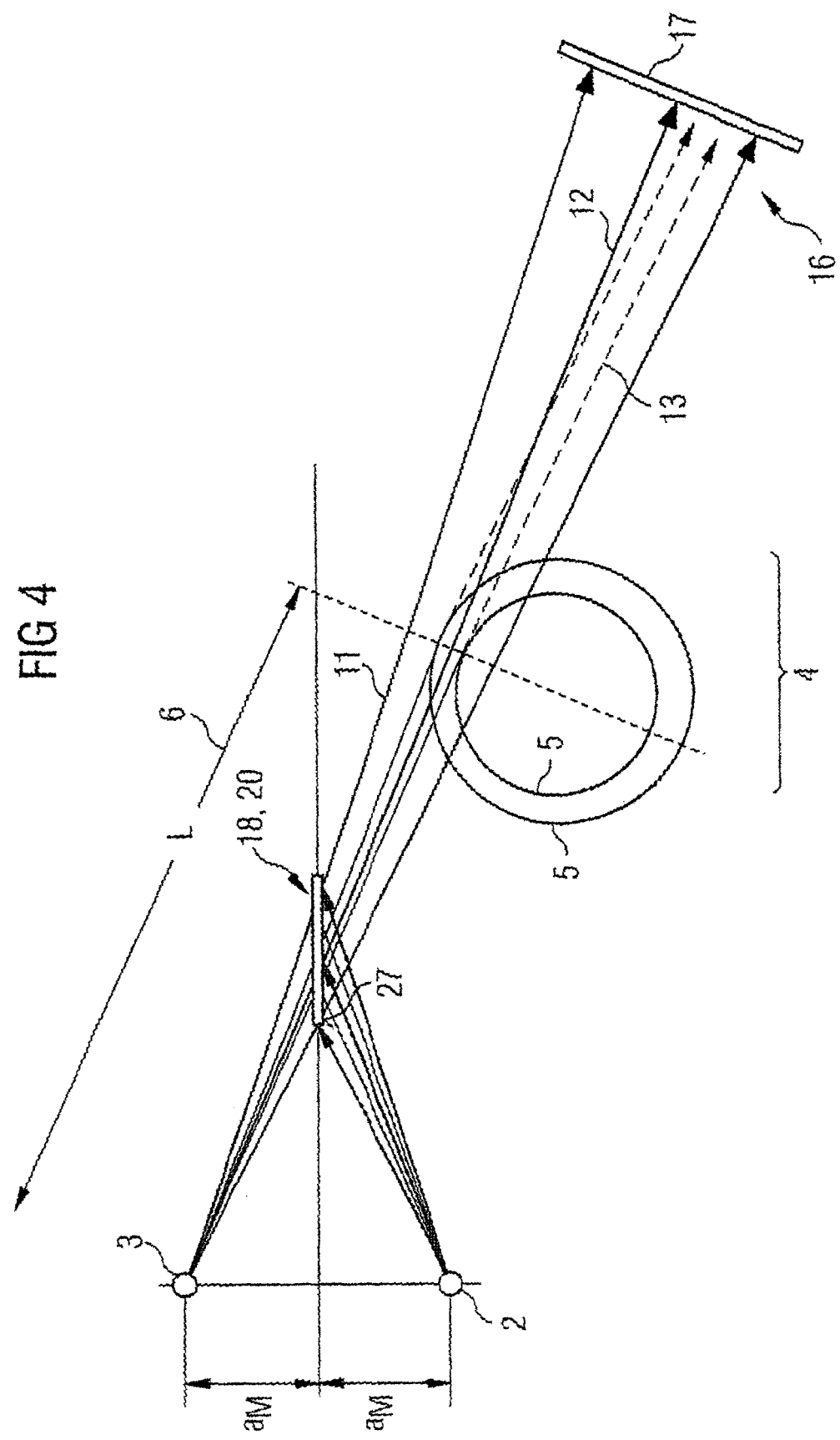
FIG. 4 shows the light path of a phase contrast X-ray device with a monochromator as a gradient multilayer reflector with a planar area of reflection.

Phase contrast X-ray device 1 with monochromator 18 as a gradient multilayer reflector 20 with a planar area of reflection 27 (FIG. 4).

Figure 3:
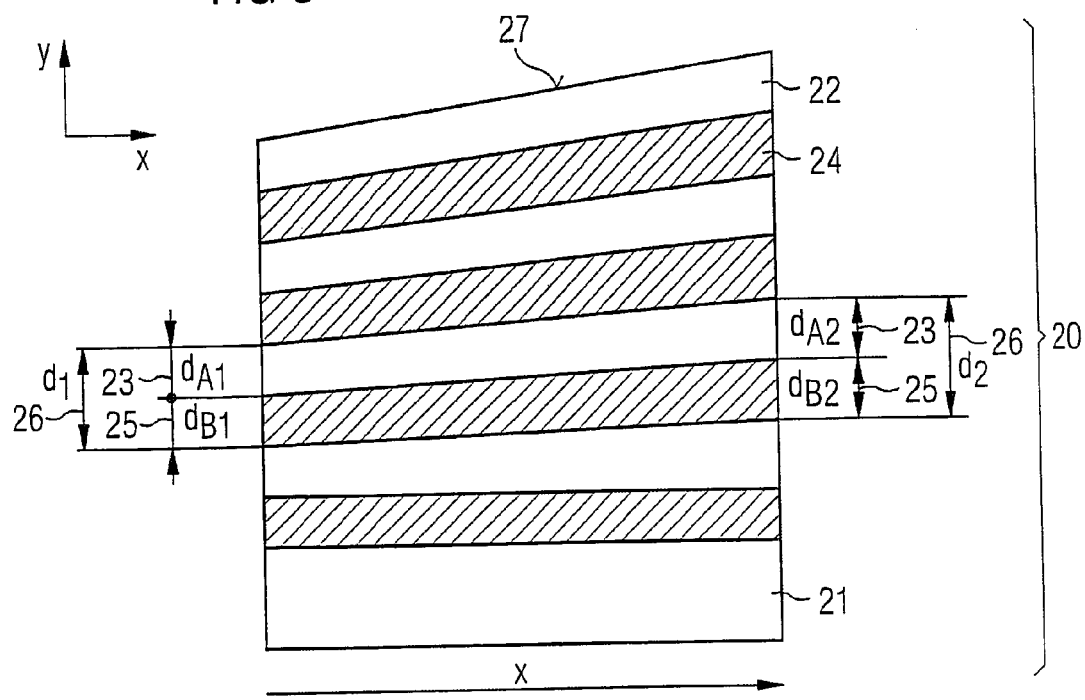
FIG. 3 shows the cross-section of a gradient multilayer reflector.

The gradient multilayer reflector 18 with a planar area of reflection 27 is shown in FIG. 3. A periodic series of layers of two layer types 22 (A) and 24 (B) is arranged on a substrate 21. The layer types distinguish themselves in each case via a refractive index $r_A$ and $r_B$ and corresponding layer thicknesses $d_A$ and $d_B$. A total layer thickness (total of the layer thicknesses $d_A$ and $d_B$) increases in a direction of propagation. The total $d_2$ exceeds the total $d_1$.

The gradient multilayer reflector 20 is arranged in the excitation light path between the X-ray source 2 and the object 4 and functions as a monochromator 18. The X-radiation reflected from the reflector 20 apparently emerges from the mirrored (virtual) X-ray source 3 and then hits the object 4 that is arranged within the optical distance 6. As a result, X-radiation of suitable spatial and temporal coherence 14 and 15 passes through the object 4. The X-radiation passes through the object 4 to the evaluation unit 16. The evaluation unit 16 has an X-ray film. The inference patterns resulting from the X-radiation passing through the object via the surface boundaries 5 are made visible on the X-ray film.

EXAMPLE 3

Figure 5:
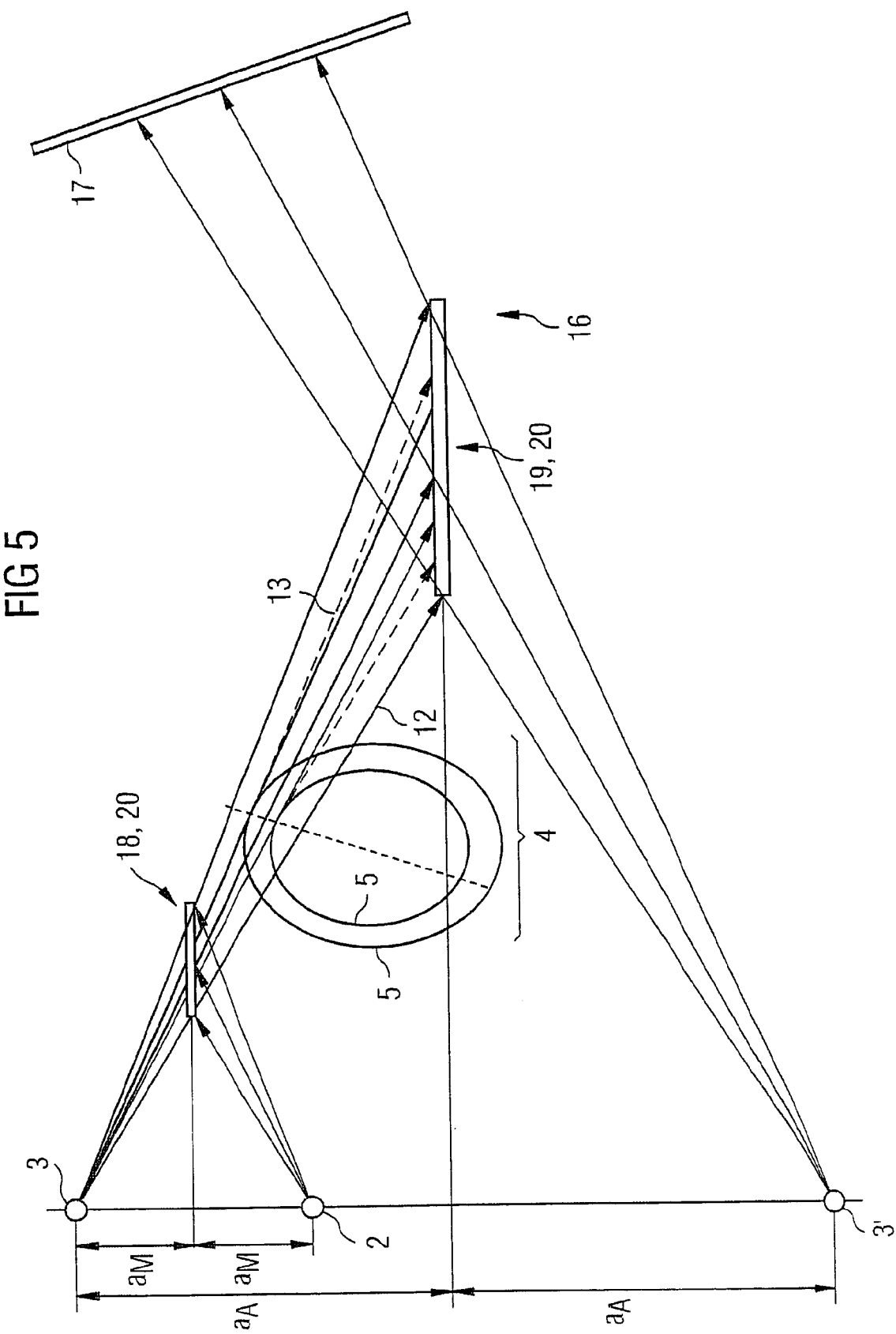
FIG. 5 shows the light path of a phase contrast X-ray device with a monochromator and an analyzer each in the form of a gradient multilayer reflector with a planar area of reflection.

Phase contrast X-ray device 1 with monochromator 18 and analyzer 19 as two gradient multilayer reflectors with planar areas of reflection 27 (FIG. 5).

In addition to the preceding example, a further multilayer reflector is arranged 20 in the light path of the X-radiation 11 between the object 3 and the evaluation unit 16. The object of the second multilayer reflector is that of an analyzer 19. Monochromator 18 and analyzer 19 form a so-called monochromator analyzer set. Monochromator 18 and analyzer 19 are arranged with areas of reflection 27 aligned parallel to one another. The analyzer 19 is designed in such a way that non-deflected X-radiation 12 arrives at the X-ray film of the evaluation unit 16 and is detected. X-radiation 13 deflected from object 4 is not reflected and does not reach the X-ray film.

Monochromator 18 and analyzer 19 have a gradient course d(x) along the direction of propagation x of the specific reflector that is aligned to the same source point 2 or its mirror images 3 and 3' and the same wave length L of the X-radiation 11. For a gradient multilayer reflector 20 with a planar area of reflection 27, the following applies to the gradient course: $d(x)=(\lambda/2)(x/a)$ with the wave length $\lambda$ of the X-radiation and the distance a of the reflector 20 from the source point of the X-ray source 2 (cf. Schuster et al., Proc. SPIE, 3767 (1999), pages 183–198). If the monochromator 18 is arranged within the distance $a_M$ and the analyzer 19 within the distance $a_A$ from the X-ray source 2, the following applies to the gradient course of the monochromator 18 $d_M(x)=(\lambda/2)(x/a_M)$ and for the gradient course of the analyzer 19 $d_A(x)=(\lambda/2)(x/a_A)$.

EXAMPLE 4

Figure 6:
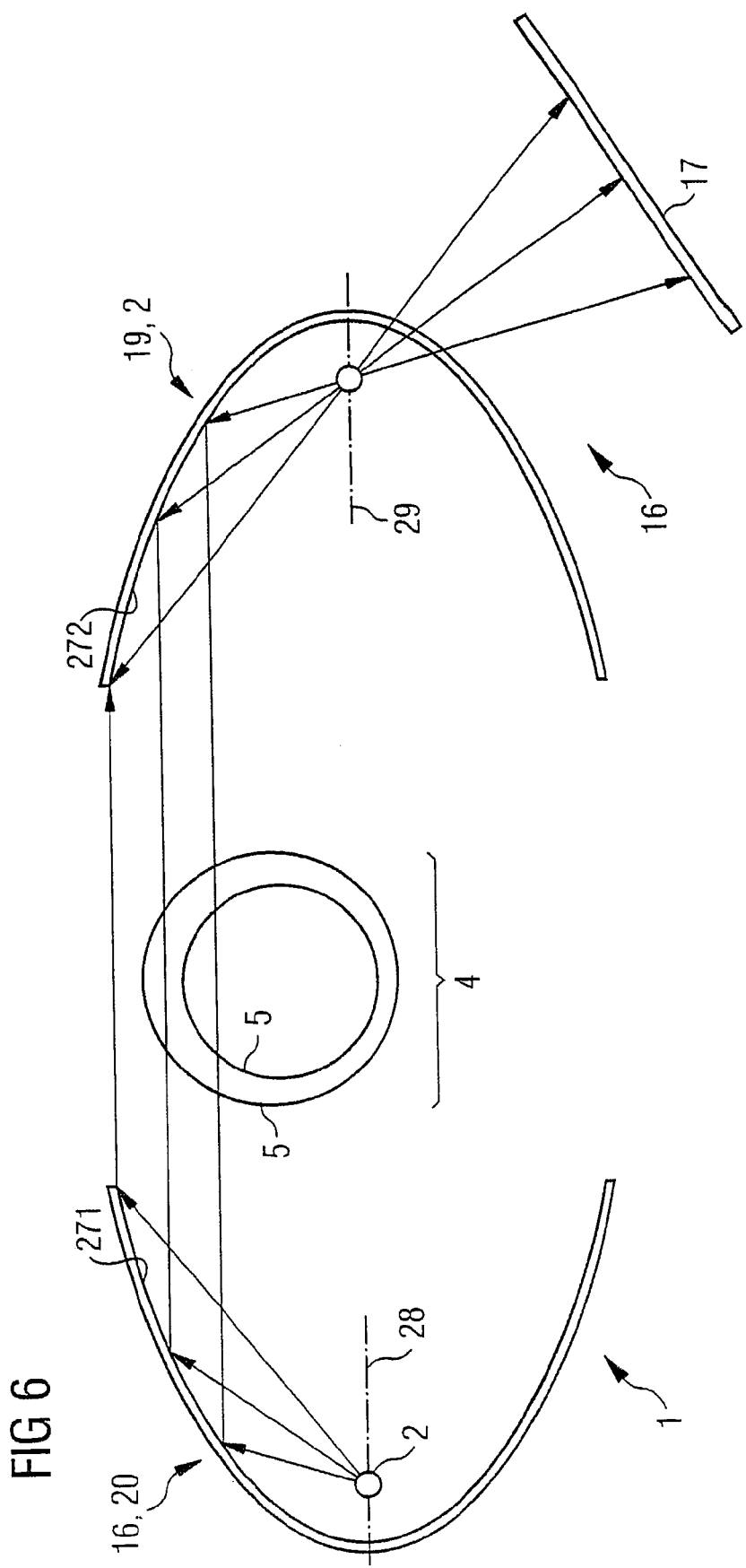
FIG. 6 in each case shows the light path of a phase contrast X-ray device with a monochromator and an analyzer each in the form of a gradient multilayer reflector with a bent area of reflection.

Phase contrast X-ray device 1 with monochromator 18 and analyzer 19 as two gradient multilayer reflectors 20 with parabolic areas of reflection 271 and 272 (FIG. 6).

The monochromator area of reflection 271 and the analyzer area of reflection 272 are arranged opposite one another in such a way that their center lines 28 and 29 are aligned parallel to one another. Unlike the preceding examples, the object 4 is in a parallel light path. The gradient course of a gradient multilayer reflector with parabolic areas of reflection is described in Schuster et al., Proc. SPIE, 3767 (1999), pages 183–198.

The monochromator analyzer set is specifically tuned to a specific wave length. Unlike the planar gradient multilayer reflectors, the wave length is hereby changed by replacing the monochromator analyzer set.

EXAMPLE 5

Phase contrast X-ray device 1 with monochromator 18 and analyzer 19 as two gradient multilayer reflectors with elliptical areas of reflection.

The gradient course of a gradient multilayer reflector with elliptical areas of reflection is described in Schuster et al., Proc. SPIE, 3767 (1999), pages 183–198.

In the same way as for gradient multilayer reflectors with parabolic areas of reflection, the monochromator analyzer set is specifically tuned to a specific wave length. The wave length is also changed here by replacing the monochromator analyzer set.

EXAMPLE 6

Phase contrast X-ray device 1 with monochromator 18 and analyzer 19 as two gradient multilayer reflectors with circular areas of reflection.

Both reflectors 20 have sharp focal circles. The gradient courses are tuned to the same wave length. The gradient course of a gradient multilayer reflector with circular areas of reflection is described in Schuster et al., Proc. SPIE, 3767 (1999), pages 183–198.

In the same way as for gradient multilayer reflectors 20 with parabolic or elliptical areas of reflection, the monochromator analyzer set is specifically tuned to a specific wave length. The wave length can also be changed here by replacing the monochromator analyzer set.

EXAMPLE 7

Phase contrast X-ray device with monochromator and analyzer as two gradient multilayer reflectors with different areas of reflection.

Such an arrangement is then, for example, possible when the light paths are taken over in the focal points of the reflectors or as a parallel ray.

The invention claimed is:

1. Phase contrast X-ray device (1) for creating a phase contrast image (17) of at least one object (4), comprising:
    at least one X-ray source (2) for generating X-radiation (11) that has a known spatial coherence (15) within a predetermined distance (6) from the X-ray source (2), and
    at least one evaluation unit (16) for converting the X-radiation (12, 13) that has passed through the object (4) that is arranged within the predetermined distance (6) from the X-ray source (2) into the phase contrast image (17) of the object (4), wherein:
    the X-ray source (2) has an output within a range of 50 W up to and including 10 kW;
    the X-radiation has a spatial coherence length (14) within the predetermined distance (6) from the X-ray source (2) in a range from 0.05 µm up to and including 10 µm;
    the X-ray source (2) has a line-shaped focus (7), a longitudinal extension of the line-shaped focus (7) being aligned in a direction towards the object (4).

2. Phase contrast X-ray device according to claim 1 in which the X-ray source (2) has an X-ray tube with a transmission anode.

3. Phase contrast X-ray device according to claim 1 in which the X-ray source (2) produces parametric X-radiation (PXR).

4. Phase contrast X-ray device according to claim 1 in which the X-ray source is constructed so as to produce X-radiation (11) that has a specific temporal coherence (15).

5. Phase contrast X-ray device according to claim 4, further comprising at least one monochromator (18) for generating the specific temporal coherence (15) of the X-radiation (11).

6. Phase contrast X-ray device according to claim 5 in which the monochromator (18) has at least one gradient multilayer reflector (20).

7. Phase contrast X-ray device according to claim 6 in which the at least one gradient multilayer reflector (20) has a periodic series of layers of a first layer type A (22) and at least a further layer type B (24) in which case the first layer type A (22) has a first refractive index $r_A$ and a first layer thickness $d_A$ (23) and a further layer type B (24), a further refractive index $r_B$ and a layer thickness $d_B$ (25) differing from the first refractive index $r_A$ and in at least one direction of propagation of the reflector (20), there is a monotone increase in layer thicknesses by a total of ($d = d_A + d_B$) (26).

8. Phase contrast X-ray device according to claim 6 in which the at least one gradient multilayer reflector (20) has at least one area of reflection (27) from at least one of the elliptical, parabolic, planar, circular, and hyperbolic groups.

9. Phase contrast X-ray device according to claim 1 in which the at least one evaluation unit (16) has at least one analyzer (19) for analyzing the X-radiation (12, 13) after it has passed through the object (4).

10. Method for creating a phase contrast image of an object comprising the steps of:
 a) providing a phase contrast X-ray device (1) for creating a phase contrast image (17) of at least one object (4), comprising:
  at least one X-ray source (2) for generating X-radiation (11) that has a known spatial coherence (15) within a predetermined distance (6) from the X-ray source (2), and
  at least one evaluation unit (16) for converting the X-radiation (12, 13) that has passed through the object (4) that is arranged within the predetermined distance (6) from the X-ray source (2) into the phase contrast image (17) of the object (4), wherein:
  the X-ray source (2) has an output within a range 50 W up to and including 10 kW;
  the X-radiation has a spatial coherence length (14) within the predetermined distance (6) from the X-ray source (2) in a range from 0.05 μm up to and including 10 μm; and
  the X-ray source (2) has a line-shaped focus (7), a longitudinal extension of the line-shaped focus (7) being aligned in a direction towards the object (4);
 b) arranging the object within the predetermined distance from the X-ray source,
 c) passing X-radiation through the object and
 d) creating the phase contrast image from where the X-radiation passes through an object by means of the evaluation unit.

11. Method according to claim 10 in which the X-radiation forms an interference pattern after it has passed through the object that is detected for creating the phase contrast image.

12. Method according to claim 10, wherein at least one of an X-radiation which is deflected when passing through the object for creating the phase contrast image and an X-radiation which is non-deflected when passing through the object is detected.

13. Method according to claim 12 in which at least one of the deflected X-radiation and non-deflected X-radiation is selected by means of an analyzer with a gradient multilayer reflector.

14. Method according to claim 10 in which several phase contrast images are created by means of the X-radiation of different spatial coherences that are processed to an overall phase contrast image by means of an image processing unit.

15. Method according to claim 14 in which the distance between the object and the X-ray source varies for generating the different spatial coherence.

16. Method according to claim 14 in which orientation of the object to the direction of propagation of the X-radiation varies for generating the different spatial coherence.

17. Method according to claim 10 in which an object that consists essentially of a material with a low absorption coefficient for the X-radiation is used.

18. Method according to claim 10 in which many phase contrast images of the object are created to generate a phase contrast computer tomogram of the object.

* * * * *